(12) United States Patent
Kincaid (10) Patent No.: US 7,894,998 B2
(45) Date of Patent: Feb. 22, 2011

(54) METHOD FOR IDENTIFYING SUITABLE NUCLEIC ACID PROBE SEQUENCES FOR USE IN NUCLEIC ACID ARRAYS

(75) Inventor: Robert Kincaid, Half Moon Bay, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 559 days.

(21) Appl. No.: 10/184,501

(22) Filed: Jun. 26, 2002

(65) Prior Publication Data

US 2004/0002070 A1      Jan. 1, 2004

(51) Int. Cl.
G06F 19/00 (2006.01)
G06G 7/48 (2006.01)
(52) U.S. Cl. .......................................... 702/20; 703/11
(58) Field of Classification Search ................... 702/19, 702/20; 435/6
See application file for complete search history.

(56) References Cited

U.S. PATENT DOCUMENTS 5,556,749 A       9/1996   Mitsuhashi et al.
6,251,588 B1 *    6/2001   Shannon et al. ................. 435/6
6,510,391 B2 *    1/2003   Balaban ....................... 702/19

FOREIGN PATENT DOCUMENTS

WO    WO-9710365 A1 *   3/1997

OTHER PUBLICATIONS

Herwig et al. "Information theroetical probe selection for hybridisation experiments" Bioinformatics (2000) vol. 16, pp. 890-898.*
Website: http://ftp.genome.washington.edu/RM/RepeatMasker.htm, entitled "RepeatMasker Documentation," p. 1-7, Jun. 12, 2002.

* cited by examiner

Primary Examiner—Eric S Dejong (57) ABSTRACT

Methods of identifying regions of a nucleic acid sequence suitable for use as probes in nucleic acid arrays, as well as compositions of matter for practicing such methods, are provided. The subject methods include: (a) providing a set of known, undesirable probe sequences; (b) comparing a nucleic acid sequence to each member of the set; and (c) identifying regions of the nucleic acid sequence that substantially match a sequence of a member of the probe set as undesirable regions. The subject methods also include marking the undesirable regions of the nucleic acid sequence to identify regions of the nucleic acid sequence that are suitable for use as probes in a nucleic acid array. The subject invention also includes an algorithm and kits for carrying out the subject methods. Also provided are nucleic acid arrays produced with the identified suitable probes, and methods for using the same.

40 Claims, 2 Drawing Sheets

METHOD FOR IDENTIFYING SUITABLE NUCLEIC ACID PROBE SEQUENCES FOR USE IN NUCLEIC ACID ARRAYS

FIELD OF THE INVENTION

The field of this invention is nucleic acid probes, specifically nucleic acid probes for use in nucleic acid arrays.

BACKGROUND OF THE INVENTION

Arrays of binding agents or probes, such as polypeptide and nucleic acids, have become an increasingly important tool in the biotechnology industry and related fields. These binding agent arrays, in which a plurality of probes are positioned on a solid support surface in the form of an array or pattern, find use in a variety of different fields, e.g., genomics (in sequencing by hybridization, SNP detection, differential gene expression analysis, identification of novel genes, gene mapping, finger printing, etc.) and proteomics.

In using such arrays, the surface bound probes are contacted with molecules or analytes of interest, i.e., targets, in a sample. Targets in the sample bind to the complementary probes on the substrate to form a binding complex. The pattern of binding of the targets to the probe features or spots on the substrate produces a pattern on the surface of the substrate and provides desired information about the sample. In most instances, the targets are labeled with a detectable label or reporter such as a fluorescent label, chemiluminescent label or radioactive label. The resultant binding interaction or complexes of binding pairs are then detected and read or interrogated, for example by optical means, although other methods may also be used depending on the detectable label employed. For example, laser light may be used to excite fluorescent labels bound to a target, generating a signal only in those spots on the substrate that have a target, and thus a fluorescent label, bound to a probe molecule. This pattern may then be digitally scanned for computer analysis.

Generally, in discovering or designing probes to be used in an array, a nucleic acid sequence is selected based on the particular gene of interest, where the nucleic acid sequence may be as great as about 60 or more nucleotides in length or as small as about 25 nucleotides in length or less. From the nucleic acid sequence, probes are synthesized according to various nucleic acid sequence regions, i.e., subsequences, of the nucleic acid sequence and are associated with a substrate to produce a nucleic acid array. As described above, a detectably labeled sample is contacted with the array, where targets in the sample bind to complimentary probe sequences of the array.

As is apparent, a key step in designing arrays is the selection of a specific probe or mixture of probes that may be used in the array and which maximize the chances of binding with target in a sample, while at the same time minimize the time and expense involved in probe discovery and design. In practice, designing an optimized array typically involves iterating the array design one or more times to replace probes that are found to be undesirable for detecting targets of interest, either due to poor signal quality and/or cross-hybridization with sequences other than the targets of interest. Such iterations are costly and time consuming.

For example, conventional probe design may be performed experimentally or computationally, where in many instances it is performed computationally. Accordingly, probe design usually involves taking subsequences of a nucleic acid and filtering them based on certain computationally determined values such as melting temperature, self structure, homology, etc., to attempt to predict which subsequences will generate probes that will provide good signal and/or will not cross-hybridize. The subsequences that remain after the filtering process are selected to generate probes to be used in nucleic acid arrays.

While attempts have been made to predict which probes will provide the best results in an array assay, such attempts are not completely satisfactory as probes selected using these methods are often still found to be undesirable for one or both of the above-described reasons. In other words, some probes will still fail or give false results as the computational techniques used to filter and select the probes are not precise predictors. Accordingly, as mentioned above, typically an array deign must be iterated a number of times in order to filter out all the undesirable probes from the array. Furthermore, such attempts often characterize probes after they have been synthesized, that is after time and expense have been already been invested.

As such, there is continued interest in the development of new methods and devices for producing arrays of nucleic acid probes that provide strong signal and do not cross hybridize with sequences other than targets of interest. Of particular interest is methods of probe selection that are easy to use, cost effective, which identify undesirable regions of the nucleic acid sequence before they are used to generate probes and which mark the undesirable regions of the nucleic acid sequence so that the undesirable regions are permanently prevented from being used to generate nucleic acid probes.

SUMMARY OF THE INVENTION

Methods of identifying regions of a nucleic acid sequence that are suitable for use as probes in nucleic acid arrays, as well as compositions of matter for practicing such methods, are provided. Embodiments of the subject methods include the following steps; (a) providing a set of known, undesirable probe sequences; (b) comparing a nucleic acid sequence to each member of the set of known, undesirable probe sequences; and (c) identifying regions of the nucleic acid sequence that substantially match a sequence of a member of the probe set as undesirable regions, whereby regions of said nucleic acid sequence that are suitable for use as probes in a nucleic acid array are identified. Embodiments of the subject methods also include marking the undesirable regions of the nucleic acid sequence such that unmarked regions that are suitable for use as probes in a nucleic acid array are identified. Also included are methods for expanding the set of known, undesirable probe sequences, for example by determining undesirable probe sequences using experimental or computational analyses. The subject invention also includes an algorithm and kits for carrying out the subject methods. Also provided are nucleic acid arrays produced with the identified suitable probes, and methods for using the same.

DEFINITIONS

In the present application, unless a contrary intention appears, the following terms refer to the indicated characteristics.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "biopolymer" refers to a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source.

The term "peptide" as used herein refers to any polymer compound produced by amide formation between a carboxyl group of one amino acid and an amino group of another group.

The term "oligopeptide" as used herein refers to peptides with fewer than about 10 to 20 residues, i.e., amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" refers to a nucleotide multimer of about 10 to 100 nucleotides in length and up to 200 nucleotides in length.

The term "polynucleotide" as used herein refers to a nucleotide multimer having any number of nucleotides.

The term "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

The term "monomer" as used herein refers to a chemical entity that can be covalently linked to one or more other such entities to form a polymer. Examples of "monomers" include nucleotides, amino acids, saccharides, peptides, other reactive organic molecules and the like. In general, the monomers used in conjunction with the present invention have first and second sites (e.g., C-termini and N-termini (for proteins), or 5' and 3' sites (for oligomers, RNA's, cDNA's, and DNA's)) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). In the art synthesis of biomolecules of this type utilize an initial substrate-bound monomer that is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more targets, i.e., components or analytes of interest.

The terms "nucleoside" and "nucleotide" refer to a subunit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

The terms "may" "optional" or "optionally" used herein interchangeably means that the subsequently described circumstance may or may not occur, so that the description includes instances where the circumstance occurs and instances where it does not.

The terms "probe", "probe sequence", "target probe" or "ligand" as used herein refer to a moiety made of an oligonucleotide or polynucleotide, as defined above, which contains a nucleic acid sequence complementary to a nucleic acid sequence present in a sample of interest such that the probe will specifically hybridize to the nucleic acid sequence present in the sample under appropriate conditions. The nucleic acid probes of the subject invention are typically associated with a support or substrate to provide an array of nucleic acid probes to be used in an array assay. The term "probe" or its equivalents as used herein refer to a compound that is "pre-synthesized" or obtained commercially, and then attached to the substrate or synthesized on the substrate, i.e., synthesized in situ on the substrate. The nucleic acid probes of the subject invention are produced, generated or synthesized according to probe sequences identified as suitable according to the subject invention that may or may not have been further tested or characterized.

The terms "reporter", "label" "detectable reporter" and "detectable label" are used herein to refer to a molecule capable of detection, including, but not limited to, radioactive isotopes, fluorescers, chemiluminescers, enzymes, enzyme substrates, enzyme cofactors, enzyme inhibitors, dyes, metal ions, metal sols, other suitable detectable markers such as biotin or haptens and the like. The term "fluorescer" refers to a substance or portion thereof which is capable of exhibiting fluorescence in the detectable range. The term "cofactor" is used broadly herein to include any molecular moiety which participates in an enzymatic reaction. Particular example of labels which may be used under the invention include, but are not limited to, fluorescein, 5(6)-carboxyfluorescein, Cyanine 3 (Cy3), Cyanine 5 (Cy5), rhodamine, dansyl, umbelliferone, Texas red, luminal, NADPH, horseradish peroxidase and α,β-galactosidase.

The terms "substrate", "support" and "solid support" are used herein to denote any solid support suitable for immobilizing one or more probes.

The terms "array", "microarray", and "biopolymeric array", unless a contrary intention appears, include any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. "Hybridizing" and "binding", with respect to polynucleotides, are used interchangeably. A "region" refers to any finite small area on the array that can be illuminated and any resulting fluorescence therefrom simultaneously (or shortly thereafter) detected, for example a pixel.

The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

The term "processor" refers to any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

DETAILED DESCRIPTION OF THE INVENTION

Methods of identifying regions of a nucleic acid sequence that are suitable for use as probes in nucleic acid arrays, as well as compositions of matter for practicing such methods, are provided. The subject methods include the following steps: (a) providing a set of known, undesirable probe sequences; (b) comparing a nucleic acid sequence to each member of the set of known, undesirable probe sequences; and (c) identifying regions of the nucleic acid sequence that substantially match a sequence of a member of the probe set as undesirable regions, whereby regions of said nucleic acid sequence that are suitable for use as probes in a nucleic acid array are identified. The subject methods also include marking the undesirable regions of the nucleic acid sequence such that unmarked regions that are suitable for use as probes in a nucleic acid array are identified. Also included are methods for expanding the set of known, undesirable probe sequences, for example by determining undesirable probe sequences using experimental or computational analyses. The subject invention also includes an algorithm and kits for carrying out the subject methods. Also provided are nucleic acid arrays produced with the identified suitable probes, and methods for using the same.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Methods

As summarized above, embodiments of the subject invention provides methods of identifying regions or subsequences on a nucleic acid sequence, based on a set of known undesirable sequences that correspond to undesirable probes. In embodiments of the subject invention, the identified, undesirable subsequences are marked or tagged such that they are prevented from being used as nucleic acid probes, i.e., they are prevented from being used to generate nucleic acid probes, in the instant probe design, as well as future probe designs. In this manner, regions or subsequences that provide suitable probes are identified. By suitable probes is meant that the probe sequence meets a predetermined specificity of binding affinity for its complement, e.g., a suitable probe provides sufficient signal for its intended use and/or does not cross-hybridize with molecules or sequences other than its complementary target. Suitability may be sample dependent such that a probe sequence may be suitable or desirable for one or more certain sample type while unsuitable or undesirable for one or more other sample types, e.g., a probe may be suitable for a sample type of human origin while unsuitable for a sample type of mouse origin. Suitability may also be based on one or more of hybridization free energies, duplex melting temperatures, tendency towards self structure and the like.

The subject methods also include periodically expanding the set of known, undesirable probe sequences with additional undesirable probe sequences, e.g., as they are uncovered or discovered using computational and/or experimental analysis (see for example steps 155 and 190 of FIG. 1), such that the chances of generating undesirable probes decreases as the set is expanded and compared to nucleic acid sequences. In other words, the set of undesirable probes is a dynamic or living set. In further describing the subject invention, methods for identifying regions of a nucleic acid sequence as suitable for use as probes in an array are described first in greater detail, followed by a description of nucleic acid arrays produced with the identified suitable nucleic acid probes and methods of using the same. Finally, algorithms and kits for use in practicing the subject methods are provided.

Figure 1:
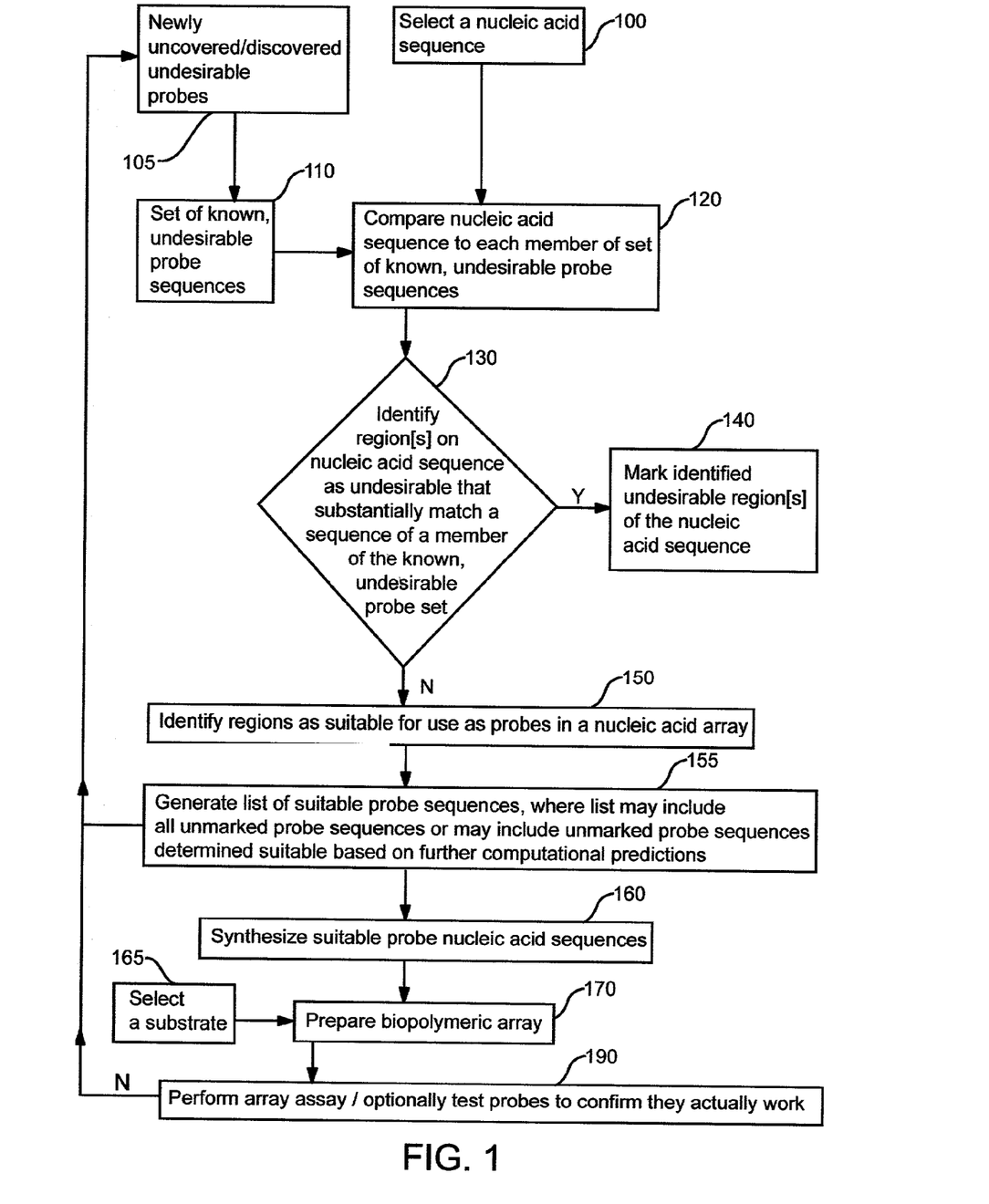
FIG. 1 shows a flowchart representing the steps of the subject methods.

Referring to FIG. 1, an exemplary embodiment of the subject methods is generally described. It will be understood that methods recited herein may be carried out in any order of the recited events, as mentioned above, and that in certain embodiments events recited herein may be omitted, changed or modified depending on the particular application at hand. As shown in FIG. 1, the subject methods include selecting a nucleic acid sequence 100, providing a set of known, undesirable probes sequences 110 and comparing each member of the set of known, undesirable probe sequences to the nucleic acid sequence 120 to identify regions or subsequences on the nucleic acid sequence that substantially match or correspond to a member of the set 130. The regions on the nucleic acid sequence identified as substantially matching a member of the set of known, undesirable probe sequences are marked 140, thereby preventing probes from being generated therefrom. As such, regions on the nucleic acid sequence that do not match a member of the set of known, undesirable probe sequences are identified as suitable for use as probes in a nucleic acid array 150. The subject methods also include generating a list of suitable probe sequences to be synthesized according to the unmarked regions, where the list may include all unmarked sequences or may include only those unmarked sequences that are further determined to be suitable based on further computational predictions or analysis 155 such as by analyzing melting temperature, self-structure, homology, etc, as is known in the art, where those probe sequences found unsuitable based on further computational predictors may then be added to the set of known, undesirable probe sequences and the probe sequences found suitable may then be used in an array assay.

In the subject methods, probe nucleic acids are synthesized, i.e., suitable nucleic acid probes, according to the regions of the nucleic acid sequence that are not identified as unsuitable based on the set of known, undesirable probe sequences, i.e., are not marked, or that have been further determined to be suitable based on further computational analyses 160, i.e., according to the list of suitable probe sequences to be synthesized, where the synthesized probes are used to prepare a biopolymeric array 170. The arrays are then used in an array assay. In certain embodiments, an array assay is used to confirm that the probes work, e.g., using experimental measurements on synthesized arrays to confirm that they actually work in such a nucleic acid array under appropriate experimental conditions. For example, a test for the consistency or selectivity of target detection may be used to test the probe sequences by contacting the array with a detectably-labeled sample and determining whether detectable signal is present when a sufficient amount of labeled target is known to be present and whether no signal is present when labeled target is absent, where the presence of a signal in the absence of labeled target indicates cross-hybridization. In such a case, the probe sequence is determined not to be selective for the target and may be added to the set of known, undesirable probe sequences.

The arrays can be prepared by in situ synthesis of the identified suitable probes on a substrate or may be prepared by synthesizing the identified suitable probes first and then attaching the pre-made suitable probes to a substrate. The arrays may then be used in an array-based assay such as a hybridization assay or the like. The subject methods also include expanding the set of known, undesirable probes 110 with additional undesirable probe members 105, e.g., as undesirable probe sequences are uncovered or discovered using computational and/or experimental analysis (see for example steps 155 and 190 of FIG. 1).

The methods of the subject invention may also be advantageously used with other known sequence analysis applications, for example, methods that can "mask" gene sequences to eliminate repetitive sequences, vector sequences, etc., from probe design consideration (see for example the website address for such repeat masking procedures which can be found by placing the term "repeatmasker.genome.washington." between the words "www" and "edu").

The subject methods for identifying regions of a nucleic acid sequence as suitable for use as probes in a nucleic acid array may be performed using the aid of a computer, i.e., in silico, or experimentally, but will typically be performed computationally with the aid of a computer such that the nucleic acid is provided in a suitable text format.

Accordingly, as described above, the subject methods include the selection of a particular nucleic acid sequence 100, from which a suitable nucleic acid probe or a mixture of suitable nucleic acid probes are produced. In many embodiments, the nucleic acid sequence is provided in text format or as a string of text, where the text represents or corresponds to the sequence of nucleotides of the nucleic acid. The nucleic acid sequence can be of any length, where the nucleic acid sequence is typically about 20 nt to about 60 nt in length. However, nucleic acid sequences of lesser or greater length may be used as appropriate. Suitable nucleic acid probes produced therefrom may be oligonucleotides or polynucleotides, as will be described in greater detail below.

Once a nucleic acid sequence is selected, a set of known, undesirable probe sequences are provided 110 and the nucleic acid sequence selected according to step 100 is compared to the set of known probe sequences that represent probes that are undesirable 120. By undesirable probe sequence it is generally meant that the undesirable probe sequence does do not meet a predetermined specificity of binding affinity for its complement, e.g., an undesirable probe may provide poor signal and/or cross-hybridize with sequences other than desired sequences, i.e., have low specificity for a target. Undesirability may be sample dependent such that a probe sequence may be desirable for one or more certain sample types, e.g., of human origin, while undesirable for one or more other sample types, e.g., of mouse origin. Such a set of undesirable probe sequences may be embodied or stored on a computer readable medium or the like in the form of textual information or text strings that represent or correspond to the nucleic acid sequences of known, undesirable probes, as will be described in greater detail below. By known in meant that the probes are proven or acknowledged to be undesirable probes for use in a nucleic acid array, e.g., empirically determined, etc.

The members of the set may correspond to any nucleic acid, e.g., DNA, mRNA, etc., depending on the particular probe design, with the only limitation being that the members of the set are able to recognize a sequence on the nucleic acid sequence that substantially corresponds or matches thereto. As such, the undesirable probe sequences may be complementary to or the same as the substantially matched sequences of the nucleic acid sequence.

As described above, the nucleic acid sequence is compared to the set of undesirable probe sequences and regions or subsequences on the nucleic acid sequence that substantially match an undesirable probe sequences are identified 130, where the comparison is usually performed computationally, i.e., with the aid of a computer such that the nucleic acid sequence and the set of known undesirable probe sequences are present in text formats representative of the nucleotide sequences thereof. By substantially match is meant that typically no more than about 5 mismatches are present, usually no more than about 2 mismatches are present and more usually no mismatched bases are present, i.e., a perfect or 100% match is present, between a member of the set and a corresponding region on a nucleic acid sequence in order to determine a substantial match. However, in certain embodiments, the number of mismatches may be greater than described above or, as mentioned, only perfect matches may be considered a substantial match.

Once a substantial match is identified, one or more regions of the nucleic acid sequence found to be a substantial match to a member of the known, undesirable probe set is marked, blocked or otherwise tagged or identified such that a probe corresponding to a marked region is prevented from being generated therefrom 140. It will be apparent that identifying subsequences or regions on a nucleic acid sequence that correspond to known, undesirable probes, i.e., identifying the subsequences before probes are produced from the nucleic acid, greatly reduces the time, expense and complexity of probe design over conventional methods known in the art which typically use computationally expensive and time consuming calculations, as described above, which usually results in probes that are undesirable being used in an array and, further, which characterize the effectiveness of the probes after synthesis thereof. Thus, according to the subject invention, regions of the nucleic acid sequence that are suitable for use as probes in an array are identified in that they are not marked because they are not identified as substantially matching a member of the known, undesirable probe set.

An identified region may be marked using any convenient protocol, with the only limitation being that the mark prevents a probe from being generated therefrom. Typically, probes are generated from the nucleic acid sequence by "chopping-up" or otherwise dividing or breaking down the nucleic acid sequence into a plurality of subsequences that are used to produce probes of corresponding sequences, i.e., probes are synthesized according to the subsequences. Using the subject methods, the regions on the nucleic acid sequence that are marked are ignored or not recognized such that they do not become one of the subsequences to which a probe is generated.

In one embodiment where the nucleic acid sequence is a text string that represents a nucleic acid such that the subject methods are carried out by way of a computer, a region identified as substantially matching an undesirable probe is marked by replacing the nucleotides represented in text format that corresponds to the identified region with a non-nucleotide marker that is not recognized or is ignored when the nucleic acid is divided to produce subsequences for probe generation.

For example, the text nucleotides of the identified subsequence may be replaced with an "N" or the like, where "N" designates an unknown, unrecognizable or ignorable base. For example, the text of a gene sequence defined by the sequence ATCGATCG is replaced with the sequence ATCNNNCG, where the sequence defined by GAT is identified as substantially matching a member of the set of undesirable probes. Accordingly, when the nucleic acid sequence is chopped-up or divided to provide sequences for probes, the sequences that include "N's" or the like are ignored and, as such, do not provide sequences for probes, e.g., do not provide sequences for further probe selection criteria. In this manner, the subsequences that are masked because they are known to be undesirable, are immediately filtered-out of the probe design while unmarked regions are identified as suitable for use as probes in a nucleic acid array.

Once all identified substantially matched regions on the target sequence are marked, a list or database of the suitable probe sequences to be synthesized is generated 155. Such a list or database may include all unmarked regions or, in many embodiments, the unmarked regions are further evaluated for suitability based on further computational predictors such as melting temperature, homology, self-structure and the like. In other words, the unmarked regions on the nucleic acid sequence may be further processed or filtered to determine suitability according to probe design algorithms known in the art to generate probe sequences.

Once a list or database of suitable probes is generated, the suitable nucleic acid probes are synthesized according to those nucleotide regions of the nucleic acid sequence that are not marked 160, i.e., according to the generated list or database of suitable probe sequences to be synthesized, where various methods for synthesizing probes are known in the art. The synthesized probes are associated with a substrate (165) to provide a biopolymeric or nucleic acid array 170.

Suitable nucleic acid probes identified according to the subject methods may be used in nucleic acid arrays such that the suitable nucleic acid probes are associated with a substrate in a particular pattern or arrangement, as will be described in greater detail below. Accordingly, the subject methods provide suitable nucleic acid probes that are capable of hybridizing with a variety of nucleic acid targets in a sample exposed to the probes, such as viral, prokaryotic and eukaryotic nucleic acids to provide duplex nucleic acids. As such, the nucleic acid sequence from which the probes are synthesized may be any convenient nucleic acid, including DNA, mRNA, nucleic acids of one or more synthetic or non-naturally occurring nucleotides, and the like.

The arrays of the subject invention may be produced using any convenient protocol, where various methods for forming arrays from pre-formed probes, or methods for generating the array using synthesis techniques to produce the probes in situ, are generally known in the art. See, for example, Southern, U.S. Pat. No. 5,700,637; Pirrung, et al., U.S. Pat. No. 5,143,854 and Fodor, et al. (1991) Science 251:767-777, the disclosures of which are incorporated herein by reference and PCT International Publication No. WO 92/10092. For example, the suitable probes may either be synthesized directly on the solid support or substrate to be used in the array assay or attached to the substrate after they are made. Arrays may be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, and 6,323,043; and U.S. patent application Ser. No. 09/302,898 filed Apr. 30, 1999 by Caren et al., and the references cited therein, the disclosures of which are herein incorporated by reference. Other drop deposition methods may be used for fabrication. Also, instead of drop deposition methods, photolithographic array fabrication methods may be used such as described in U.S. Pat. Nos. 5,599,695, 5,753,788, and 6,329,143, the disclosures of which are herein incorporated by reference. As mentioned above, interfeature areas need not be present, particularly when the arrays are made by photolithographic methods as described in those patents.

Accordingly, in one instance, probes corresponding to the unmarked regions of the nucleic acid may be synthesized in situ, using standard methods of sequential nucleotide phosphoramidite addition on a substrate. That is, suitable probe nucleic acids are synthesized on a surface of a support. Alternatively, the suitable probes may be synthesized by conventional chemosynthetic techniques, e.g., phosphoramidite chemistry, or by biosynthetic techniques, e.g., polymerase chain reaction "PCR", and attached to a substrate, i.e., probe nucleic acids are deposited on a surface of a support (in other words the probes are made pre-made and then deposited on a surface), where the probes may be printed onto the support, spotted, etc., as is known in the art. See, for example, Brown T. et al. Oligonucleotides and Analogues A Practical Approach; and Schena M. et al. Science; U.S. application Ser. No. 09/354,816 entitled "Methods and Compositions for Producing Biopolymeric Arrays"; as well as WO 98/41531 and the references cited therein for synthesizing polynucleotides, the disclosures of which are herein incorporated by reference.

The probe nucleic acids of the subject invention, i.e., the suitable nucleic acid probes, are typically oligonucleotides, and as such will generally be at least about 10 nt in length, and will usually range from about 10 to about 100 nt in length, where the oligonucleotide probes may be as long as about 100 to about 200 nucleotides in length or even more in certain embodiments.

The suitable nucleic acid probes of the subject invention are used in nucleic acid arrays 170, as mentioned above, to detect one or more target molecules, usually labeled target molecules, in a sample exposed to the array, where such arrays and methods of using the arrays will be described in detail below.

In many embodiments of the subject invention, the probe nucleic acids synthesized from unmarked regions of a nucleic acid sequence are tested in an array hybridization assay to confirm that the synthesized probe nucleic acids actually work in a nucleic acid array 190. In other words, the synthesized suitable probes are further screened to confnim their suitability as nucleic acid probes. As such, such synthesized probe nucleic acids may be characterized as "candidate" probe nucleic acids in that they are further evaluated for suitability as probes in a nucleic acid array.

Confirmation of the candidate probe nucleic acids may include any suitable protocol for determining the suitability of probe nucleic acids for use in a particular array. In one such protocol, following an array hybridization assay whereby an array of candidate probe nucleic acids is exposed to a sample having labeled target molecules, the array is read to detect the presence of duplexes formed on the array surface between probe and target molecules, as will be described in greater detail below. Accordingly, to confirm that the nucleic acid probes work in a nucleic acid array, various factors may be evaluated such as binding specificity, melting temperatures, hybridization energies and signal quality or signal strength. Once the candidate probes are further filtered, those selected by the filtering process are then used in an array for use in an array-based assay while the probe(s) found not to be suitable by this step may then be added to the set of known, undesirable probe sequences.

The subject methods also include expanding or adding to the set of known, undesirable probes 110 with newly discovered undesirable probe sequences 105. That is, the set is periodically updated to include recently uncovered or discovered undesirable probe sequences not already represented in the set, such that the set is a dynamic or changeable, i.e., expandable, set. For example, a researcher may discover an undesirable probe in the course of research, using computational and/or experimental techniques, that is not already represented in the set. Accordingly, the set is then updated to include the recently discovered undesirable probe sequence. It will be apparent that in this manner, the chances of identifying probes that are suitable for use in an array increases every time the set is increased because the nucleic acid sequence is compared to a larger number of known, undesirable probe sequences.

Nucleic Acid Arrays and Methods of Using the Same

As mentioned above, subsequences on the nucleic acid identified as suitable for use as probes in a nucleic acid array according to the subject methods are used to generate probe nucleic acids. That is, the unmarked regions of the nucleic acid provide the sequences to which probes are synthesized, where such sequences may be further filtered using computational methods.

Accordingly, the subject invention also includes nucleic acid arrays that include nucleic acid probes identified as suitable for use in arrays according to the methods described above. That is, suitable nucleic acid probes are synthesized according to the regions on a nucleic acid sequence identified to provide suitable nucleic acid probes. Generally, these probes are deposited onto the surface of a substrate in the form of an "array" or pattern. Such arrays find use in a variety of applications, including gene expression analysis, drug screening, nucleic acid sequencing, mutation analysis, and the like.

The subject biopolymeric arrays include at least two distinct polymers that differ by monomeric sequence attached to different and known locations on the substrate surface. Each distinct polymeric sequence of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 cm$^2$ or even less than about 10 cm$^2$. For example, features may have widths (that is, diameter, for a round spot) in the range from about 10 µm to about 1.0 cm. In other embodiments, each feature may have a width in the range from about 1.0 µm to about 1.0 mm, usually from about 5.0 µm to about 500 µm and more usually from about 10 µm to about 200 µm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

Figure 2:
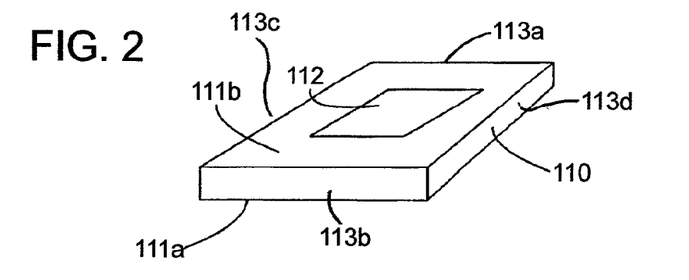
FIG. 2 shows an exemplary substrate carrying an array, such as may be used in the devices of the subject invention.
Figure 3:
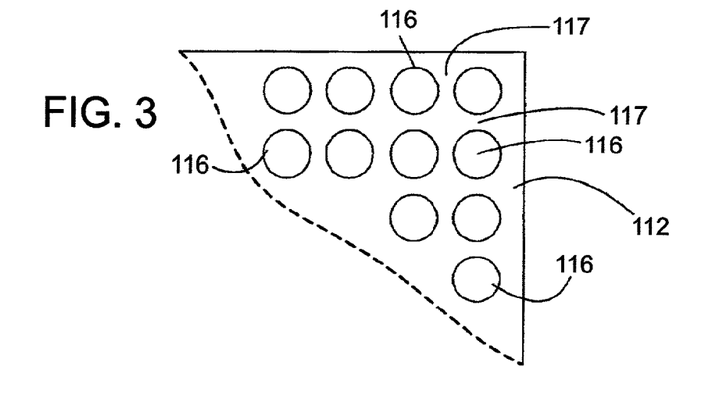
FIG. 3 shows an enlarged view of a portion of FIG. 2 showing spots or features.
Figure 4:
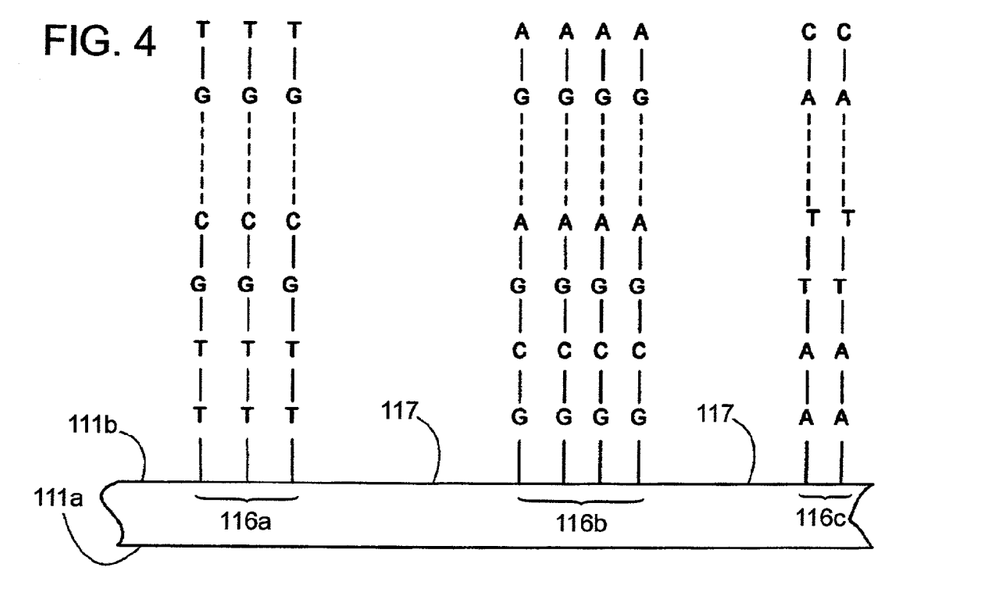
FIG. 4 is an enlarged view of a portion of the substrate of FIG. 3.

Referring to FIGS. 2-4, typically arrays of the present invention use a contiguous substrate 110, usually a planar substrate, carrying an array 112 of probe nucleic acids identified as suitable according to the subject methods disposed on a rear surface 111b of substrate 110. It will be appreciated though, that more than one array (any of which are the same or different) may be present on rear surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111b, with regions of the rear surface 111b adjacent the opposed sides 113c, 113d and leading end 113a and trailing end 113b of substrate 110, are usually not being covered by any array 112. A front surface 111a of the substrate 110 typically does not carry any arrays 112. Each array 112 may be designed for testing against any type of sample, whether a trial sample, reference sample, a combination of them, or a known mixture of biopolymers such as polynucleotides.

Substrate 110 may carry on front surface 111a or any other convenient location, an identification code (not shown), e.g., in the form of bar code or the like, printed on a substrate in the form of a paper label attached by adhesive or any convenient means. The identification code contains information relating to array 112, where such information may include, but is not limited to, an identification of array 112, i.e., layout information relating to the array(s), etc.

In practice, substrate 110 may be of any shape and size. Accordingly, the shape of the substrate shown herein is for exemplary purposes only and is in no way intended to limit the scope of the invention. A variety of solid supports or substrates may be used, upon which an array may be positioned. In certain embodiments, a plurality of arrays may be stably associated with one substrate. For example, a plurality of arrays may be stably associated with one substrate, where the arrays are spatially separated from some or all of the other arrays associated with the substrate.

The substrate may be selected from a wide variety of materials including, but not limited to, natural polymeric materials, particularly cellulosic materials and materials derived from cellulose, such as fiber containing papers, e.g., filter paper, chromatographic paper, etc., synthetic or modified naturally occurring polymers, such as nitrocellulose, cellulose acetate, poly (vinyl chloride), polyamides, polyacrylamide, polyacrylate, polymethacrylate, polyesters, polyolefins, polyethylene, polytetrafluoro-ethylene, polypropylene, poly(4-methylbutene), polystyrene, poly(ethylene terephthalate), nylon, poly(vinyl butyrate), cross linked dextran, agarose, etc.; either used by themselves or in conjunction with other materials; fused silica (e.g., glass), bioglass, silicon chips, ceramics, metals, and the like. For example, substrates may include polystyrene, to which short oligophosphodiesters, e.g., oligonucleotides ranging from about 5 to about 50 nucleotides in length, may readily be covalently attached (Letsinger et al. (1975) Nucl. Acids Res. 2:773-786), as well as polyacrylamide (Gait et al. (1982) Nucl. Acids Res. 10:6243-6254), silica (Caruthers et al. (1980) Tetrahedron Letters 21:719-722), and controlled-pore glass (Sproat et al. (1983) Tetrahedron Letters 24:5771-5774). Additionally, the substrate can be hydrophilic or capable of being rendered hydrophilic.

Suitable substrates may exist, for example, as sheets, tubing, spheres, containers, pads, slices, films, plates, slides, strips, disks, etc. The substrate is usually flat, but may take on alternative surface configurations. The substrate can be a flat glass substrate, such as a conventional microscope glass slide, a cover slip and the like. Common substrates used for the arrays of probes are surface-derivatized glass or silica, or polymer membrane surfaces, as described in Maskos, U. et al., Nucleic Acids Res, 1992, 20:1679-84 and Southern, E. M. et al., Nucleic acids Res, 1994, 22:1368-73.

Each array may cover an area of less than about 100 cm$^2$, or even less than about 50 cm$^2$, 10 cm$^2$ or 1 cm$^2$. In many embodiments, the substrate carrying the one or more arrays will be shaped generally as a rectangular solid (although other shapes are possible), having a length of more than about 4 mm and less than about 1 m, usually more than about 4 mm and less than about 600 mm, more usually less than about 400 mm; a width of more than about 4 mm and less than about 1 m, usually less than about 500 mm and more usually less than about 400 mm; and a thickness of more than about 0.01 mm and less than about 5.0 mm, usually more than about 0.1 mm and less than about 2 mm and more usually more than about 0.2 and less than about 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least about 20%, or about 50% (or even at least about 70%, 90%, or 95%), of the illuminating light incident on the substrate as may be measured across the entire integrated spectrum of such illuminating light or alternatively at 532 nm or 633 nm.

Immobilization of the probe to a suitable substrate may be performed using conventional techniques. See, e.g., Letsinger et al. (1975) *Nucl. Acids Res.* 2:773-786; Pease, A. C. et al., *Proc. Nat. Acad. Sci. USA,* 1994, 91:5022-5026. and "Oligonucleotide Synthesis, a Practical Approach," Gait, M. J. (ed.), Oxford, England: IRL Press (1984). The surface of a substrate may be treated with an organosilane coupling agent to functionalize the surface. See, e.g., Arkins, "Silane Coupling Agent Chemistry," *Petrarch Systems Register and Review*, Eds. Anderson et al. (1987) and U.S. Pat. No. 6,258,454.

As mentioned above, array 112 contains multiple spots or features 116 of probe nucleic acids identified as suitable according to the above-described methods, i.e., suitable nucleic acid probes in the form of polynucleotides, oligonucleotides, etc. In certain embodiments, array 112 is made of candidate probe nucleic acids, as described above, for testing the candidate probes for confirmation that they actually work in a nucleic acid array.

As mentioned above, all of the features 116 may be different, or some or all could be the same. The interfeature areas 117 could be of various sizes and configurations. Each feature carries a predetermined probe nucleic acid sequence such as a predetermined oligonucleotide or polynucleotide (which includes the possibility of mixtures of oligonucleotides and polynucleotides). It will be understood that there may be a linker molecule (not shown) of any known types between the rear surface 111b and the first nucleotide.

The subject nucleic acid arrays find use in a variety of different applications or array-based assays, where such applications are generally analyte detection applications in which the presence of a particular analyte or target in a given sample is detected at least qualitatively, if not quantitatively. Protocols for carrying out such assays are well known to those of skill in the art and need not be described in great detail here. Generally, a sample suspected of including the target or analyte of interest is contacted with an array produced according to the subject invention under conditions sufficient for the target to bind to its respective binding pair member that is present on the array. Thus, if the target of interest is present in the sample, it binds to the array at the site of its complementary binding member and a complex is formed on the array surface. The array is then read and the presence of this binding complex on the array surface is then detected, e.g., through use of a detectable label or reporter, e.g. an isotopic or fluorescent label present on the target, etc. The presence of the target in the sample is then deduced from the detection of binding complexes or duplexes on the substrate surface.

Specifically, a sample of target nucleic acids is first prepared, where preparation may include labeling of the target nucleic acids with a detectable label, e.g., a member of signal producing system. Following sample preparation, the sample is contacted with the array under stringent hybridization conditions, whereby complexes are formed between target nucleic acids that are complementary to probe sequences attached to the array surface, i.e., duplex nucleic acids are formed on the surface of the substrate by the interaction of the probe nucleic acid and its complement target nucleic acid present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Specific hybridization assays of interest which may be practiced using the subject arrays include: gene discovery assays, differential gene expression analysis assays; nucleic acid sequencing assays, and the like. U.S. patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the nucleic acid arrays are arrays of polypeptide binding agents, e.g., protein arrays, specific applications of interest include analyte detection/proteomics applications, including those described in: U.S. Pat. Nos. 4,591,570; 5,171, 695; 5,436,170; 5,486,452; 5,532,128; and 6,197,599; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

As mentioned above, in certain embodiments, undesirable probe sequences may be defined as those sequences determined undesirable for use with one or more particular sample types, e.g., human sample type, and as such regions on the nucleic acid sequence matching the undesirable sample-type probe sequences are not used in an array intended to be used with that particular sample type, in this case a human sample. In this manner, the array will include only those probes determined suitable for the particular sample type used with the array.

As mentioned above, in certain embodiments, the nucleic acid arrays of the subject invention are tested to confirm that the probes actually work. In such instances, the arrays of candidate probes are analyzed experimentally in an array assay, as described above. Accordingly, to confirm that the nucleic acid probes work in a nucleic acid array, various factor may be evaluated such as binding specificity, melting temperatures, hybridization energies and signal quality or signal strength. Once the candidate probes are further filtered, those selected by the filtering process, i.e., those confirmed that they actually work, are then used in an array for use in an array-based assay while the probe(s) found not to be suitable by this step may then be added to the set of known, undesirable probe sequences.

In certain embodiments, the subject methods include a step of transmitting data, e.g., from at least one of the detecting and deriving steps as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the at least one array may be accomplished by illuminating the at least one array and reading the location and intensity of resulting fluorescence at each feature of the array to obtain a result. For example, a scanner may be used for this purpose which is similar to the MICROARRAY SCANNER available from Agilent Technologies, Palo Alto, Calif. Other suitable apparatus and methods for reading an array are described in U.S. patent application Ser. No. 20/087,447 "Reading Dry Chemical Arrays Through The Substrate" by Dorsal et al., Ser. No. 09/846,125 "Reading Multi-Featured Arrays" by Dorsel et al.; and Ser. No. 09/430,214 "Interrogating Multi-Featured Arrays" by Dorsel et al., the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,251,685; 6,221,583, the disclosure of which is herein incorporated by reference, and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array 112 (such as whether or not a particular target sequence may have been present in the sample or whether or not a pattern indicates a particular condition of an organism from which the sample came). The results of the reading (whether further processed or not) may be forwarded (such as by communication) to a remote location if desired, and received there for further use (such as further processing).

Computer Readable Media

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

More specifically, computer readable medium may include stored programming embodying an algorithm for carrying out the subject methods. Accordingly, such a stored algorithm is configured to, or is otherwise capable of, allowing a researcher or the like to compare each member of the set of known, undesirable probe sequences to a nucleic acid sequence to identify regions or subsequences on the nucleic acid sequence that substantially match or correspond to a member of the set and mark or tag such regions, thereby preventing probes from being generated according to the marked regions so as to identify regions that correspond to suitable probes. The algorithm may also include steps or functions necessary to generate nucleic acid probes from regions of the nucleic acid sequence that are not marked.

The subject invention also includes a data set of known, undesirable probe sequences stored on a computer readable medium usable by a researcher or the like for identifying suitable probes. As described above, the stored data is configured so that it may be updated or expanded to store additional undesirable probe sequences. The data may be stored or configured in a variety of arrangements known to those of skill in the art. The data set of known, undesirable probe sequences may by stored on the same or different computer readable medium as the above-described stored programming that includes an algorithm for carrying out the subject methods. As such, the data set of known, undesirable probes may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

In one embodiment of the subject invention, a system of the invention may include a single computer or the like with a stored algorithm capable of carrying out suitable probe identification methods of the invention and may also include a stored data set of known, undesirable probe sequences. In another embodiment, a system of the invention may include a single computer or the like with a stored algorithm capable of carrying out suitable probe identification methods of the invention that is configured to access a server or database that includes the data set of known, undesirable probe sequences.

Kits

Finally, kits for use in identifying regions of a nucleic acid sequence as suitable for use as probes in a nucleic acid array. Such kits at least include an algorithm present on a computer readable medium for carrying out the subject methods, together with instructions for using the algorithm to identify regions of a nucleic acid sequence as suitable for use as probes in a nucleic acid array. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, or the like. The subject kits may also include a data set of known, undesirable probes present on a computer readable medium and instructions for using the data set to identify suitable probes. The computer readable medium may be the same or different computer readable medium than that which has an algorithm stored thereon.

In certain embodiments, the kits also include one or more substrates for use in a nucleic acid array. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the subject arrays for carrying out an array based assay. The instructions may recite particular sample types to be used with the array. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, or the like.

It is evident from the above description and discussion that the above described invention provides an easy and effective way to identify regions of a nucleic acid sequence as suitable for use as probes in a nucleic acid array. The above described invention provides a number of advantages, including ease of use, cost effectiveness, identification of undesirable regions of a nucleic acid sequence before they are used to generate nucleic acid probes, and marking of undesirable regions of the nucleic acid sequence so that nucleic acid probes are prevented from being generated therefrom. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying candidate probe sequences for a nucleic acid sequence for use as probes in a nucleic acid array, said method comprising:
   (a) providing a set of known, undesirable probe sequences present in a format representative of the nucleotide sequences of said known, undesirable probe sequences, wherein said set of undesirable probe sequences comprises probe sequences that do not meet a predetermined specificity of binding affinity for said nucleic acid sequence;
   (b) comparing said nucleic acid sequence present in a format representative of the nucleotide sequence of said nucleic acid sequence to each member of said set;
   (c) marking regions of said nucleic acid sequence that have no more than 5 mismatches with a sequence of a member of said set as undesirable regions for candidate probe sequences for said nucleic acid sequence;
   (d) identifying candidate probe sequences for said nucleic acid sequence for use as probes in a nucleic acid array from unmarked regions of said nucleic acid sequence; and
   (e) synthesizing at least one of said identified candidate probe sequences.

2. The method according to claim 1, further comprising computationally analyzing one or more of said candidate probe sequences for suitability for use as probes for said nucleic acid sequence in a nucleic acid array.

3. The method according to claim 2, further comprising adding any candidate probe sequences found unsuitable to said set of known, undesirable probe sequences.

4. The method according to claim 1, further comprising synthesizing and testing one or more of said candidate probe sequences in an array hybridization assay for suitability for use as probes for said nucleic acid sequence in a nucleic acid array.

5. The method according to claim 4, further comprising adding said candidate probe sequences found unsuitable to said set of known, undesirable probe sequences.

6. The method according to claim 4, wherein said step of testing comprises determining at least one of the signal strength, binding specificity, melting temperature and hybridization energies of said synthesized candidate probe sequences.

7. The method according to claim 1, further comprising expanding said set of known, undesirable probe sequences with an additional sequence.

8. The method according to claim 1, further comprising testing an identified candidate probe sequence.

9. The method according to claim 8, further comprising adding a tested candidate probe sequence to said set of known, undesirable probe sequences.

10. The method according to claim 8, wherein said testing is accomplished using experimental analysis.

11. The method according to claim 8, wherein said testing is accomplished using computational analysis.

12. The method according to claim 8, wherein said testing is based at least in part on a particular sample type.

13. The method of claim 8, wherein said format is a computer readable format.

14. The method of claim 8, wherein said method further comprises employing said identified candidate probe sequences in the manufacture of a nucleic acid array.

15. A method of identifying candidate probe sequences for a nucleic acid sequence for use as probes in a nucleic acid array, said method comprising:
(a) providing a set of known, undesirable probe sequences present in a format representative of the nucleotide sequences of said known, undesirable probe sequences, wherein said set of undesirable probe sequences comprises probe sequence that do not meet a predetermined specificity of binding affinity for said nucleic acid sequence;
(b) comparing said nucleic acid sequence present in a format representative of the nucleotide sequence of said nucleic acid sequence to each member of said set; and
(c) marking regions of said nucleic acid sequence that have no more than 2 mismatches with a sequence of a member of said set as undesirable regions for candidate probe sequences for said nucleic acid sequence;
(d) identifying candidate probe sequences for said nucleic acid sequence for use as probes in a nucleic acid array from unmarked regions of said nucleic acid sequence; and
(e) synthesizing at least one of said identified candidate probe sequences.

16. The method according to claim 15, further comprising computationally analyzing one or more of said candidate probe sequences.

17. The method according to claim 15, further comprising synthesizing and testing one or more of said candidate probe sequences in an array hybridization assay.

18. The method according to claim 17, wherein said step of testing comprises determining at least one of the signal strength, binding specificity, melting temperature and hybridization energies of said synthesized candidate probe sequences.

19. The method according to claim 15, further comprising testing an identified candidate probe sequence.

20. The method according to claim 19, wherein said testing is accomplished using experimental analysis.

21. The method of claim 19, wherein said method further comprises employing said identified candidate probe sequences in the manufacture of a nucleic acid array.

22. A method of identifying candidate probe sequences for a nucleic acid sequence for use as probes in a nucleic acid array, said method comprising:
(a) providing a set of known, undesirable probe sequences present in a format representative of the nucleotide sequences of said known, undesirable probe sequences, wherein said set of undesirable probe sequences comprises probe sequences that do not meet a predetermined specificity of binding affinity for said nucleic acid sequence;
(b) comparing said nucleic acid sequence present in a format representative of the nucleotide sequence of said nucleic acid sequence to each member of said set; and
(c) marking regions of said nucleic acid sequence that have no mismatches with a sequence of a member of said set as undesirable regions for candidate probe sequences for said nucleic acid sequence;
(d) identifying candidate probe sequences for said nucleic acid sequence for use as probes in a nucleic acid array from unmarked regions of said nucleic acid sequence; and
(e) synthesizing at least one of said identified candidate probe sequences.

23. The method according to claim 22, further comprising further computationally analyzing one or more of said candidate probe sequences.

24. The method according to claim 22, further comprising synthesizing and testing one or more of said candidate probe sequences in an array hybridization assay.

25. The method according to claim 24, wherein said step of testing comprises determining at least one of the signal strength, binding specificity, melting temperature and hybridization energies of said synthesized candidate probe sequences.

26. The method according to claim 22, further comprising testing an identified candidate probe sequence.

27. The method according to claim 26, wherein said testing is accomplished using experimental analysis.

28. The method of claim 26, wherein said method further comprises employing said identified candidate probe sequences in the manufacture of a nucleic acid array.

29. The method of claim 1, wherein said format of said known, undesirable probe sequences and said format of said nucleic acid sequence are computer readable formats and said comparing, marking and identifying steps are performed by a processor.

30. The method of claim 29, further comprising presenting said identified candidate probe sequences in text format to a user.

31. The method of claim 15, wherein said format of said known, undesirable probe sequences and said format of said nucleic acid sequence are computer readable formats and said comparing, marking and identifying steps are performed by a processor.

32. The method of claim 15, further comprising presenting said identified candidate probe sequences in text format to a user.

33. The method of claim 22, wherein said format of said known, undesirable probe sequences and said format of said nucleic acid sequence are computer readable formats and said comparing, marking and identifying steps are performed by a processor.

34. The method of claim 33, further comprising presenting said identified candidate probe sequences in text format to a user.

35. The method of claim 1, wherein regions of said nucleic acid sequence that are marked are prevented from being used to generate candidate probes.

36. The method of claim 15, wherein regions of said nucleic acid sequence that are marked are prevented from being used to generate candidate probes.

37. The method of claim 22, wherein regions of said nucleic acid sequence that are marked are prevented from being used to generate candidate probes.

38. The method of claim 1, wherein said format of said known, undesirable probe sequences and said format of said nucleic acid sequence is a text format.

39. The method of claim 15, wherein said format of said known, undesirable probe sequences and said format of said nucleic acid sequence is a text format.

40. The method of claim 22, wherein said format of said known, undesirable probe sequences and said format of said nucleic acid sequence is a text format.

* * * * *

UNITED STATES PATENT AND TRADEMARK OFFICE
CERTIFICATE OF CORRECTION

| | | |
|---|---|---|
| PATENT NO. | : 7,894,998 B2 | Page 1 of 1 |
| APPLICATION NO. | : 10/184501 | |
| DATED | : February 22, 2011 | |
| INVENTOR(S) | : Robert H. Kincaid | |

It is certified that error appears in the above-identified patent and that said Letters Patent is hereby corrected as shown below:

On the face page, in field (54), in "Title", in column 1, line 1, de lete "METHOD" and insert -- METHODS --, therefor.

On the face page, in field (75), in "Inventor", in column 1, line 1, delete "Robert Kincaid" and insert -- Robert H. Kincaid --, therefor.

On the face page, in field (56), under "Other Publications", in column 2, line 1, delete "theroetical" and insert -- theoretical --, therefor.

In column 1, line 1, delete "METHOD" and insert -- METHODS --, therefor.

In column 22, line 36, in Claim 32, delete "claim 15," and insert -- claim 31, --, therefor.

Signed and Sealed this
Third Day of May, 2011

David J. Kappos
*Director of the United States Patent and Trademark Office*